United States Patent [19]
Mouton et al.

[11] Patent Number: 5,789,174
[45] Date of Patent: Aug. 4, 1998

[54] DETECTION OF PERIODONTAL PATHOGENS INCLUDING BACTEROIDES FORSYTHUS, PORPHYROMONAS GINGIVALIS, PREVOTILLA INTERMEDIA AND PREVOTELLA NIGRESCENS

[75] Inventors: Christian Mouton, Quebec, Canada; Emmanuelle Guillot, Toulouse, France; Christian Menard, Sainte-Foy, Canada

[73] Assignee: Universite Laval, Quebec, Canada

[21] Appl. No.: 729,447

[22] Filed: Oct. 11, 1996

[51] Int. Cl.$^6$ .............................. C12Q 1/68; C07H 21/02
[52] U.S. Cl. .................................. 435/6; 536/23.1
[58] Field of Search .................... 435/6; 935/77, 935/78; 536/23.1

[56] References Cited

PUBLICATIONS

Dzink et al., *J. Clin. Periodontal.* 15:316–323, 1988.
Loesche et al., *J. Clin. Microbiol.* 30:418–426, 1992.
Olsvik et al., 1994, *Clinical Microbiology reviews* 7:43–54.
Moore et al., *J. Clin. Periodontol.* 18:729–739, 1991.
Socransky et al., *J. Periodont. Res.* 26: 195–212, 1991.
Welsh et al., *Nucleic Acids Res.* 18: 7213–7218, 1990.
Williams et al., *Nucleic Acids Res.* 18:6531–6535, 1990.
Sambrook, J. et al. (1989) *Molecular Cloning: A Laboratory Manual*, 2d Ed., Cold Spring Harbor Lab., Cold Spring Harbor, N.Y.

*Primary Examiner*—Eggerton A. Campbell
*Attorney, Agent, or Firm*—Klauber & Jackson

[57] ABSTRACT

The present invention relates to probes and primers for the detection of periodontal pathogens such as *Bacteroides forsythus*, *Porphyromonas gingivalis*, *Prevotella intermedia* and *Prevotella nigrescens*. As well, the invention relates to rapid and sensitive methods for the detection and identification of periodontal pathogens from an oral sample taken from a patient. Diagnostic kits for the detection and identification of periodontal pathogens in an oral sample from a patient, are also disclosed.

19 Claims, 10 Drawing Sheets

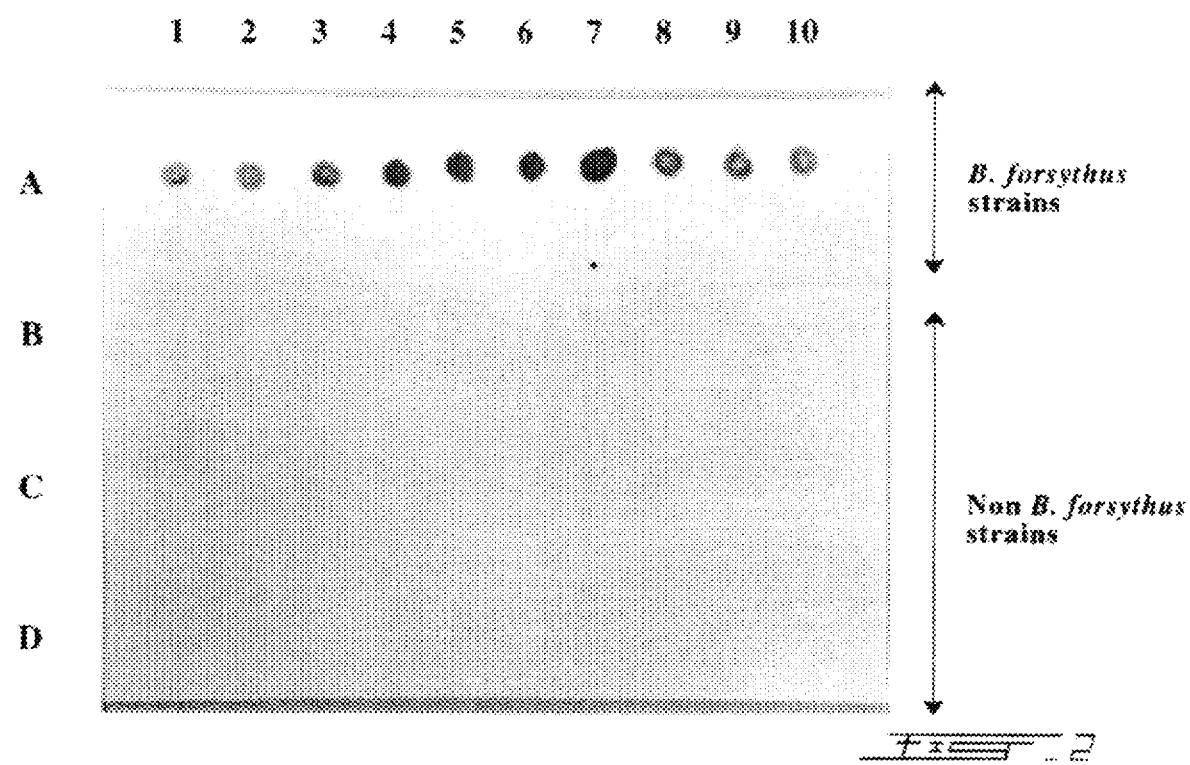

1    CAGGCCCTTC ATAATCCATG TCGATATACA AGGCGATGGC TTCGTGCAGT
51   CCGGGATGCT CCTGCTGGGT CTGTTTGAGG TATTCGATAC CGTAATCGTG
101  CTGCGCTTTA GTCCATGCAA CGACTTCGGG ATTTCCTTA TCTTCGAGCC
151  AGCGGAACGG ATCGGTGATC ACCACGTTAT GCAACGTATC TTTTACGGGT
201  TTTTGAAGAG TCACCGGGGG GCGAAACGCT ACTTGAGCGT AAGAGGTCAC
251  TGTCATGGTC AAAGTAAGTG GAAACATGAA AAAATTCTTC ATCTNCAATT
301  GTATTTTTGA ATAAGTTTGT TTTTGTGTNC AACATAGAT AAAAAGCTG
351  AGATTAAATA TGGAAAAGAA GATAAATCTC GGACGCGGTT TTCTTTTTC
401  GGAGAAAATG ATGTACCTTT GCATTGCTA AACGATCCGA AGTGTCGGAT
451  ATGGTTAAAT CATAGAGGTG ATTTCAAAT CATTACTTT TTATAGAAGG
501  GCCTGAA

FIG. 3

```
1    GTAAGGCCGG CATTCAGGTG AAAATCGTAA CGGGCGACAC ACCGGGTACC
51   GCCCGGAGAT CGGCCGCCAA ATAGGACTGT GGGACGAAAG CTGTACGGAG
101  CGGAATATGA TCACCGGTTC GCCCTCACCG ACGAGGAACT
151  GCGCCCTCGG ATAGGCGAAC TGCGTATCAT GTCCGCGCTC GTCGATGGAC
201  AAGGAAAGGC TTGTACGCCT GCTGCAGGAA GGCTCGCGGA GGTGGTGGCC
251  GTGACGGGCG ACGGCACGAA CGACGCTCCT GCACTCAACC GCGCACAGGT
301  GGGCCTCTCG ATGGGCGATG GCACTGCGTA GCCAAAGAGG CGAGCGACAT
351  CACCATTCTG GACAATTCTT TCAGCAGCAT TGCCAAAGCC GTTATGTGGG
401  GACGATCGCT TTATCGGAAT ATCCGCCCGTT TTATCCTCTT TCAGATGACC
451  ATCAACGTCG TGGCCTGTAT CATCGTTCTG ATCGGCGCAT TTGTGGGTAC
501  GGAGTCGCCC CTTACCGTGA CGCAAATGCT GTGGGTCAAT CTCATCATGG
551  ACACTTTCGC CGCCCTTGTCC TCCCTCCCGA CAAGGGTGTG
```

*Fig-4A*

```
 601  ATGAAGGAGC AACCCCGCCG GCAGGACGAT GCCATCATCA ACCCGCTGAT
 651  GGCACGACGA ATTTTCGGGC TTGGCGGAGG ATTCGTTTTG CTGCTCTTCA
 701  GCCTGATCCA ATACTTCAAA CATGCCGAAC TCAACAGCAT GATGGACTTC
 751  CACCTCGGTG CATGCTACTG CCCTCTTCGA CTTCCGGCCT GTAGAGAATG
 801  CTCTTCCGA CTTTGAGCTG AGTGCATTCT TCTCCATATT CGTTTCCCTC
 851  CAATTCTGGT ATATGTTCAA CGCCAAAGCA TTTATGACAG GGCGGAGGCC
 901  CTGCACCGGC TGTGGAAATG TCGCAACTTC GTCATCATCG CCCTGCTGAT
 951  TCTTATAGAC AAATCATCAT CACGACTTTT GGCGGAGGCA TGTTCGGTAG
1001  TACCCCTTGC CCGATGGAC TGGATTCTCA TCATCCCTCGC GACGAGTCTG
1051  ATCCTCTGGT TGCGCGAATT GGAACGCATA TTGCCTACTT TTGCAAATCA
1101  TCTTATTCAT AATCGACAAT AATGAAAAAA GCTATTCTTT CCGGAGCGGC
1151  CTTAC
```

FIG. 4B

```
1    CAGCACCCAC AACGATATGA TCTGCCACAG CTTTTGAACC ATTATGTTCA
51   GCACTTACAC TTGCCAACAA CATTATATCG TCCCATGGCA AATAGCCAAC
101  TTTGNCTCA AGCCCGATAT TGAACTTATC GTGCCCGTTA TAGTGCAAGT
151  CAAGACCTGT CAAAGAAGCT CCAAGGTAGC CTTTACCCTC TTGAAACTGT
201  GCATGAATAC CTAATGATAA TGTTAATCCT AATAAAAGGA GGGATAATTT
251  CTTCATCATA ATAATACTGT TATTGTAAAA TCTATTTATT GCTAAATTCC
301  ATTGACAAAG GTAGTAGAAA TATTTGAATT ACAAAAATTA TTGCCTATCT
351  TTGTGCCTGA TTTGCAAATA AGTCCCTTCGC TTTCTTGCTT ACAAATATGC
401  TTTAAAACGT ATGAATAAAA AATTAATTAC ACTGATATTA CTAAGCTGTC
```

FIG. 5A

451 TTCACGATAA ATTGTTTTGC ACAAACGGGC GAAATATTTA TAAATTGGGA

501 TACAAAACCT TTCAAGAAAC GTGAAACCCG TGCTGTTTGG CTAACTACTT

551 TGAACAATCT TGACTGGCCA AAGACATTTG CAAACTCGGA GNGAGGTATT

601 GAAAGACAAA AGCAGGAACT CATTGATATT TTAGATAAAT ATGTCGCTGC

651 AAACATTAAT ACCGTTCTGT TGCAAACGCG TGTGCGTGCA GCCACCATTT

701 ATCCGTCCAA CATAGAACCT TGGGACAAAT GCTTGACAGG CAGAGAAGAT

751 GGAAATCCAA ACTACGACCC ATTGGCATTT GCTGTTGAAG AATGCCATAA

801 ACGTGGGTTG GAAATACATG CGTGGGTGCT G

FIG. 5B

5'CAGCACCCCACCACGGAACGCGATACGACCGGGGAAAGTTGGCTTTTTATGTTACCCGTTATGATG
GAAGTAGTTGGGCGTTGTGTTGCTATAATCATGTGAATGCCTACCGCACGCGCCAGCTGGGCGAT
ACGGGTGATAGGCATTTCAATTTCTTTTCCAGCGGTAAGGATAAGGTCTCCGAACTCATCAATGA
TGACAACGATGTACGGTATGAACTCGTGTCCCCGCAGGACTAAGCTGATGGCTAAGGAACTTC
TTGTTATACTCTTTTATATTGCGCGCTCCTGTAG....unknown sequence of
approx.700bp....AAATTAAGGGTTGGATACTNCCAATTGGGGAAAGGTTCGTGTGGATTAA
TAGGTGTTNCAAGGTCTCGTGCCTGCCACCCCCTTACCTTGTGCCTTTTCCAACCCGACAGGG
ACATTAACTTTCATTCCTATTTCGCCTTCTCTTTCATCGTTCTCTTTCGCCGTGGT
TTTGTCCCTTAGCGTTAGGCTTTATCATGGTATTTGGCAGGTCATCGTCAAGAAATTCCACCGTCT
GGGACTCTCTGCATTCTGCAGCTTTTCTACTGCTTCCTCCCTCCATTTCGTGGGTGCTG3'

FIG. 6

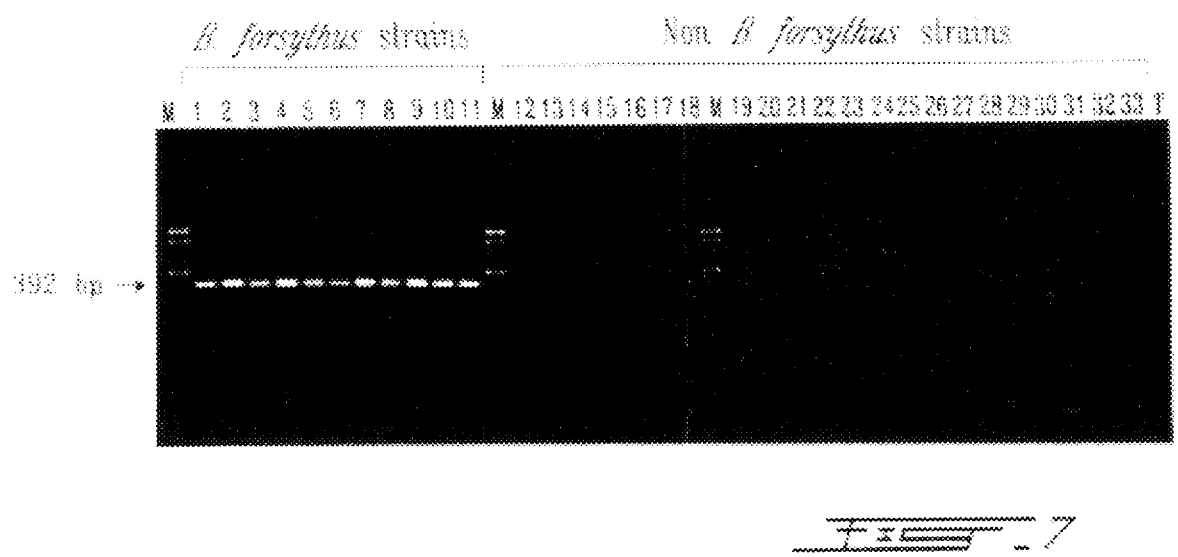

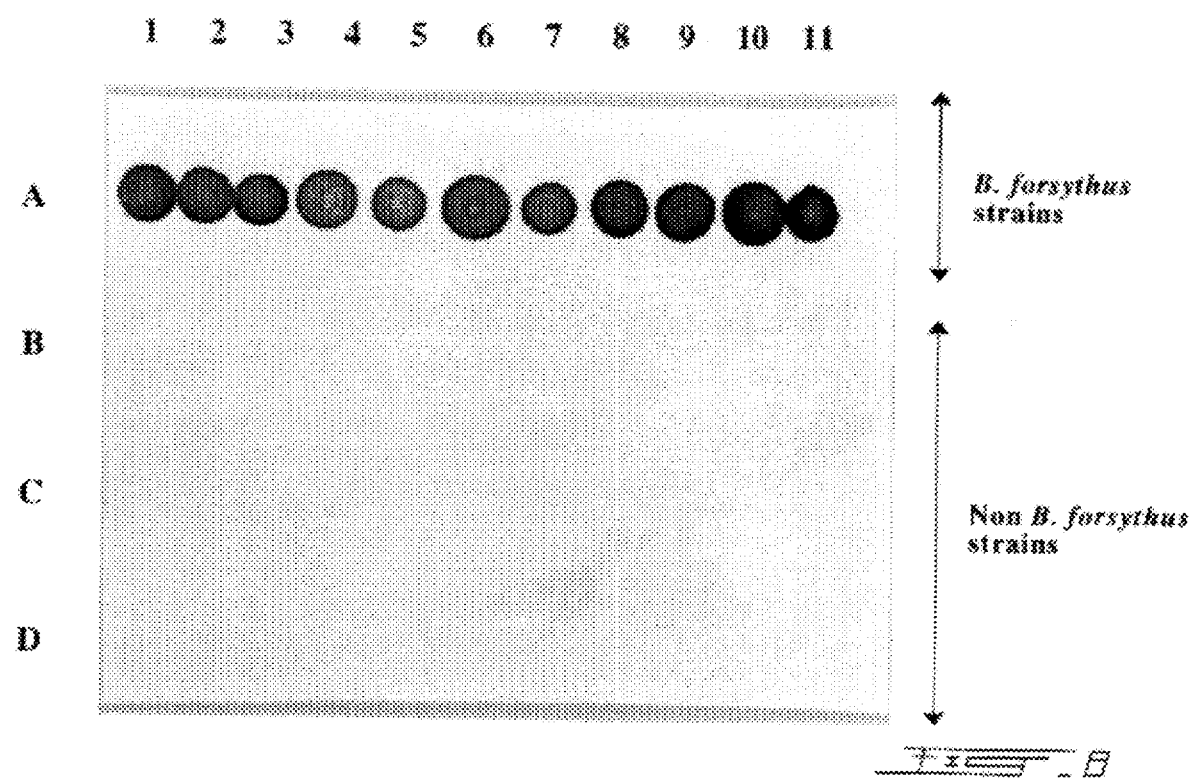

DETECTION OF PERIODONTAL PATHOGENS INCLUDING BACTEROIDES FORSYTHUS, PORPHYROMONAS GINGIVALIS, PREVOTILLA INTERMEDIA AND PREVOTELLA NIGRESCENS

BACKGROUND OF THE INVENTION (a) Field of the Invention

The invention relates to probes for the detection of periodontal pathogens such as Bacteroides forsythus, Porphyromonas gingivalis, Prevotella intermedia and Prevotella nigrescens. The invention further relates to primers for the sensitive detection of periodontal pathogens. As well, the invention relates to rapid and sensitive methods for the detection and identification of periodontal pathogens from an oral sample taken from a patient. In addition, the present invention relates to kits for the detection and identification of periodontal pathogens in an oral sample from a patient.

(b) Description of Prior Art

The concept that bacteria, in particular Gram negative anaerobes, initiate the major mechanisms of destruction of the periodontium (the supporting tissues of the tooth, consisting of the gingivae, periodontal ligament, alveolar bone and ligament) has received convincing scientific support in recent years (Socransky et al., 1991, J. Periodont. Res. 26:195–212). These bacteria are packed in a dense mass of cells with close physical contact, referred to as subgingival plaque. Studies to identify etiologic agents by culturing plaque samples from periodontal pockets have consistently revealed that periodontitis is a polymicrobial infection in which hundreds of taxa can be detected. Periodontal infections are thus quite different from the generally monomicrobial infections at other sites of the body, for which diagnosis and treatment fit the postulate "one microorganism, one pathology". Since the microbiota consists of facultative and strict anaerobic bacteria the periodontal infections are considered mixed infections. Studies of the predominant cultivable oral microbiota have helped to realize that different complexes of micro-organisms are found in supragingival and subgingival plaques, that the bacteria in healthy sites differ remarkably from those found in periodontal pockets, that transition from health to disease is associated with a shift from a predominantly Gram positive, facultative flora to a predominantly Gram negative, anaerobic flora, and that some species rather than others are predominant in active sites. Among the 150 to 200 different species that any individual may typically harbor, perhaps as few as 10 to as many as 30 species are frequently associated with active destruction (Dzink et al., 1988, J. Clin. Periodontol. 15:316–323; and Moore et al., 1991, J. Clin. Periodontol. 18:729–739). It is now commonly accepted that only approximately 20 species (see Table 1), known as putative periodontopathic bacteria, may regularly play a role in the pathogenesis of destructive periodontal diseases because of their high frequency of isolation and pathogenic potential. Among these, Bacteroides forsythus, Porphyromonas gingivalis, Prevotella intermedia and Prevotella nigrescens are considered key pathogens.

TABLE 1

| Periodontal pathogens | |
|---|---|
| Gram negative species | Gram positive species |
| Actinobacillus actinomycetemcomitana | Actinomyces |

TABLE 1-continued

| Periodontal pathogens | |
|---|---|
| Gram negative species | Gram positive species |
| | A. viscosus |
| | A. naeslundii |
| Bacteroides forsythus | Streptococcus intermedius |
| Campylobacier rectus | Peptostreptococcus |
| Eikenella corrondens | P. anaerobius |
| Eubacterium | P. micros |
| E. alactolyticum | |
| E. brachy | |
| Fusobacterium | |
| F. alocis | |
| F. nucleatum | |
| Porphyromonas gingivalis | |
| Prevotella | |
| P. intermedia | |
| P. nigrescens | |
| Selenomonas sputigena | |
| Treponema | |
| T. denticola | |
| T. socranskii | |

The anaerobic cultural procedure has been seen as inadequate on a routine basis as certain of the putative periodontal pathogens are either uncultivable or extremely difficult to cultivate (Loesche et al., 1992, J. Clin. Microbiol. 30:418–426). In addition, cultivation techniques are time-consuming and expensive, they require highly trained technicians and specialized equipment and have many sources of method error. The inability to reliably culture the putative periodontal pathogens calls for substitute bacteriological diagnostic procedures that are specific, sensitive and fast, such as nucleic acid probe tests.

The choice of DNA probe to be used in a test is obviously critical. A total chromosomal probe is extremely complex and, by nature, unlikely to be specific in terms of sequence for a particular organism; consequently, chromosomal probes often cross-react with related species which makes them unsuitable for diagnostic use in polymicrobial infections. This is a matter of special concern in periodontics, considering that the taxonomic status of most putative periodontal pathogens is occasionally uncertain: so-called "cryptic" species are regularly found within a taxon, which, as long as they remain ignored, confuse the search for etiologic agents. For example, a new pigmented species, Prevotella nigrescens, hitherto unrecognized within the species Prevotella intermedia has been identified.

Probes designed using a specific sequence selected from the genome of a pathogen, as synthetic oligonucleotide probes 19–50 bases long, are generally considered preferable to whole genome probes. However, the preparation of such oligonucleotides requires knowledge of the target sequence. Sequence data from a number of strains of the organism of interest must therefore be obtained to ensure the selection of a genetically stable target region, a labor and time intensive effort.

The sequences of genes encoding rRNA, for instance the subunit 16S of the ribosomal RNA (16S rRNA), can be used to develop DNA probes. The ubiquitous nature of these genes and the presence of variable domains in the rRNA that allow to select specific DNA sequences make it possible to develop species-specific DNA probes. However, this method still requires elaborate sequence determination. In addition 16S rRNA are highly conserved and sometimes cannot distinguish bacteria at the species level.

Randomly cloned fragments of chromosomal DNA have also been proposed to develop species-specific probes. However, the laborious methodology that is required precludes their extensive use.

Although the hybridization techniques using nucleic acid probes are very useful, the lack of sensitivity is a major drawback, and microbial populations consisting of $10^4$ bacteria per ml or lower usually cannot be detected accurately. In order to be able to detect bacteria present in numbers below this threshold the target DNA must be amplified in vitro, for instance by the polymerase chain reaction (PCR), which allows to detect microbes down to a few cells per ml. A disadvantage of the use of typical PCR methods however, is the fact that knowledge of the sequence of the target nucleic acid is initially required.

Molecular methods for bacterial diagnosis in periodontology are still in their infancy, since the construction of probes by traditional methods has been hampered by the fact that prior knowledge of the nucleic acid sequence to be used as a target was required. Indeed, it must be recalled that, unlike specific infectious diseases, periodontal diseases are highly polymicrobial infections, and that the number of probes to be constructed, each recognizing a likely etiologic agent, is correspondingly great.

Novel approaches to the rapid design and construction of DNA probes which require no preliminary knowledge of the genetics of the target organisms to speed up the generation of desirable probes would thus provide a significant advantage to the dental community, including researchers and clinicians. Indeed it would be beneficial for the clinician to have tools available for the specific identification of the periodontopathic bacteria, particularly *Bacteroides forsythus, Porphyromonas gingivalis, Prevotella intermedia* and *Prevotella nigrescens*.

SUMMARY OF THE INVENTION

One aim of the present invention is to provide means to detect and identify periodontopathic bacteria in a sample from a patient and more particularly *Bacteroides forsythus, Porphyromonas gingivalis, Prevotella intermedia* and *P. nigrescens*.

Another aim of the present invention is to provide means to detect and identify quickly and specifically, periodontopathic bacteria in a sample from a patient without having prior knowledge of the sequence of the nucleic acid from the targeted periodontopathic bacteria.

Another aim of the present invention is to provide probes and/or primers for the rapid and sensitive detection of periodontopathic bacteria and more particularly *Bacteroides forsythus, Porphyromonas gingivalis, Prevotella intermedia* and *Prevotella nigrescens*.

Another aim of the present invention is to provide a method of deriving probes and primers for the rapid and sensitive detection of periodontal bacteria, as well as a sensitive method for detecting and identifying periodontopathic bacteria such as *Bacteroides forsythus, Porphyromonas gingivalis, Prevotella intermedia* and *Prevotella nigrescens*. The methods being based on (i) the identification of a first generation or "anonymous" probe, obtained without a need for prior knowledge of nucleic acid sequence information from the targeted bacterial species; (ii) determination of the sequence of the anonymous probe and derivation therefrom of a second generation probe which is a shorter sequence internal to that of (i), and (iii) design of primers that allow DNA amplification of the anonymous probe, the second generation probe or subsets thereof, with (i), (ii) and (iii) being specific for the targeted periodontopathic bacteria.

Another aim of the present invention is to provide a means to increase the sensitivity of the detection method by using an immuno-capture step, as a means to concentrate the targeted periodontopathic bacteria.

Yet another aim of the present invention is to provide kits for the detection and/or identification of periodontopathic bacteria such as *Bacteroides forsythus, Porphyromonas gingivalis, Prevotella intermedia* and *Prevotella nigrescens* in an oral sample from a patient.

A desirable development in non-culture methods for the diagnosis of bacterial infections is the combination of DNA amplification and probe-mediated identification with the constraint that the construction of nucleic probes requires no prior knowledge of the genetics of the target organisms. An additional benefit can be contemplated in that both nonviable and noncultivable bacterial species can be detected.

The non-culture methods of the present invention for the detection and identification of periodontal bacterial species are based on the use of a species-specific genetic marker, identified as such among polymorphic products known as RAPDs for Random amplified polymorphic DNAs (Williams et al., 1990, *Nucleic Acids Res.* 18:6531–6535) in fingerprints generated by a procedure known as arbitrarily primed PCR (AP-PCR), a polymerase chain reaction at low thermal stringency primed by a single arbitrarily selected oligonucleotide (Welsh et al., 1990, *Nucleic Acids Res.* 18:7213–7218).

In accordance with the present invention there is provided an anonymous probe for the specific detection and identification of periodontopathic bacteria, wherein the probe is obtained using specific primers with nucleic acid from a targeted periodontopathic strain, to yield a nucleic acid fragment which is specific for the targeted strain, wherein the targeted strain comprise *Bacteroides forsythus, Porphyromonas gingivalis, Prevotella intermedia* and *Prevotella nigrescens*.

In accordance with the present invention there is also provided a composition of polynucleotide probes for the detection of bacteria associated with periodontal disease, wherein the probes are selected from at least one anonymous probe specific for bacterial strains associated with periodontal disease and capable of selectively hybridizing under stringent hybridizing conditions with the nucleic acid from the bacteria associated with periodontal disease.

In accordance with the present invention there is also provided primers for the detection of bacteria associated with periodontal disease, wherein said primers are derived from the sequence of the anonymous probes specific for bacteria associated with periodontal disease, and permit an amplification of a nucleic acid fragment specific for a particular species or type of bacteria associated with periodontal disease, under PCR conditions.

In addition, in accordance with the present invention there is provided a method for detecting in a sample obtained from the mouth of a human patient, bacteria associated with periodontal disease, the method comprising the steps of: contacting the bacteria present in the sample with at least one anonymous probe specific for a bacteria associated with periodontal disease, under conditions that will release the nucleic acid therefrom and that will permit a selective hybridization of the nucleic acid with the anonymous probe;

and detecting hybridization complexes as an indication of the presence of the bacteria in the sample.

In accordance with the present invention there is also provided a method of detecting in a sample obtained from the mouth of a human patient, bacteria associated with periodontal disease, the method comprising the steps of: contacting the bacteria present in the sample with a pair of primers derived from the sequence of one of an anonymous probe specific for bacteria associated with periodontal disease, under conditions that will release the nucleic acid therefrom and that will permit a selective hybridization of the nucleic acid with the primers; amplifying the nucleic acid using PCR technology; and detecting the specifically amplified PCR product characteristic of a specific bacteria associated with periodontal disease.

In accordance with the present invention there is also provided a diagnostic kit for use in determining the presence of a specific polynucleotide sequence, which comprises in a container a synthetic oligonucleotide probe comprising a selective sequence complementary to a specific anonymous probe or portion thereof of a bacteria associated with periodontal disease; wherein the specific polynucleotide sequence comprises in whole or in part anonymous probes specific for a bacteria associated with periodontal disease, or combinations thereof. In an other embodiment, the present invention provides a diagnostic kit for use in determining the presence of a specific polynucleotide sequence, which comprises in a container synthetic oligonucleotide primers complementary to a specific sequence of an anonymous probe, the anonymous probe being specific for a bacteria associated with periodontal disease.

In addition to *Bacteroides forsythus*, *Porphyromonas gingivalis*, *Prevotella intermedia* and *Prevotella nigrescens*, the present invention also concerns the other bacteria which are found to be associated with periodontal disease (see Table 1).

From the specification and appended claims, it should be understood that the nucleic acid probes and primers include synthetically derived or recombinant nucleic acid sequences, composed of DNA or RNA. The term probe is meant to include both single stranded and double stranded nucleic acid. The term probe does not necessarily imply the nucleic acid sequence is labeled, since according to one embodiment of the present invention, the first generation or second generation probes or a subset thereof, can be under certain conditions, visualized directly on a gel. In addition, the term composition should be understood to mean that a species-specific probe and/or species-specific primers may be in a pure state or in combination with other probes and/or primers. These other probes and/or primers may be specific to the same or different species. Furthermore, the probes and/or primers may be in combination with salts or buffers, and may be in a dried state, in solution or as a precipitate.

From the specification and appended claims, it should be understood that the detection of a nucleic acid segment, specific for a bacteria associated with periodontal disease (such as a species-specific PCR product) can be effected in some cases by a direct visualization of the specific nucleic acid segment, without a need for a labeling means.

Since the taxonomy of periodontal bacteria is not static, it should be understood that newly identified groups or subgroups could be used as herein described for the method of deriving probes and primers for the rapid and sensitive detection of periodontal bacteria, to derive a species-specific anonymous probe, and derive primers and probes therefrom for the rapid and sensitive detection of these newly identified bacterial groups or subgroups.

From the specification and appended claims, it should be understood that although it is preferred that each species-specific probe hybridizes to the nucleic acid of the targeted bacterial species or type, it is conceivable that hybridization conditions could be found (by modifying temperature or ionic strength for example) that permit the detection and/or identification of other bacterial species or types.

BRIEF DESCRIPTION OF THE DRAWINGS

Having thus generally described the nature of the invention, reference will now be made to the accompanying drawings, showing by way of illustration a preferred embodiment thereof, and wherein:

FIG. 2 shows a dot-blot assay demonstrating the specificity of the 507 bp anonymous probe for the species *Bacteroides forsythus*;

FIG. 3 shows the sequence of the anonymous probe identified by AP-PCR with primer OPA-01 in the species *Bacteroides forsythus*;

FIG. 4 shows the sequence of the anonymous probe identified by AP-PCR with primer 970-11 in the species *Porphyromonas gingivalis*;

FIG. 5 shows the sequence of the anonymous probe identified by AP-PCR with primer OPA-13 in the species *Prevotella intermedia*;

FIG. 6 shows the partial sequence of the anonymous probe identified by AP-PCR with primer OPA-13 in the species *Prevotella nigrescens*, as sequences of the stretches at the 3' and 5' ends of the anonymous probe.

FIG. 7 shows an agarose gel profile of the PCR assay using genomic DNA with the primer pair Bf 392-1/Bf 392-2, specific for *Bacteroides forsythus*; and FIG. 8 shows a dot blot analysis of the combined PCR-DNA probe assay with *Bacteroides forsythus*.

DETAILED DESCRIPTION OF THE INVENTION

Figure 1:
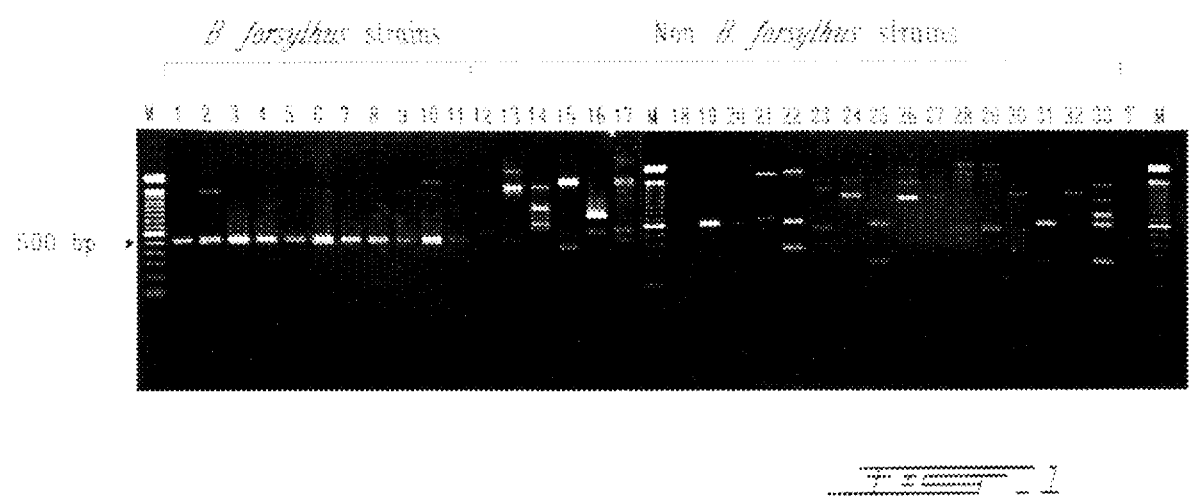
FIG. 1 shows RAPD fingerprints obtained by AP-PCR with primer OPA-01 on genomic DNA from 11 strains of *Bacteroides forsythus* and 22 strains of related and unrelated species.

The present invention relates to probes and primers which have been designed to be specific for the detection and identification of periodontopathic bacteria, without a need for the initial knowledge of the nucleic acid sequence of the targeted nucleic acid. Due the selection of species-specific probe and the validation of this specificity, the probes and primers of the present invention are superior to previously identified probes in terms of specificity. In addition, the present invention which is relatively simple and rapid, provides a level of sensitivity and specificity that had yet to be attained in a method of detection and identification of periodontal pathogens in a sample of a patient. This sample can be saliva, tooth scrapings, subgingival or supragingival material or gingival tissue.

DERIVATION OF A SPECIES-SPECIFIC ANONYMOUS PROBE

1. Collection of Strains: Large Clinical and Geographical Diversity

For each target species under study, a collection of strains that mirrors the diverse clinical situations from which the species can be isolated, must be built. Preferably, the collection should contain strains from different areas in the world, must be built so as to obtain the largest spectrum of diversity within the taxon. This is usually achieved by adding to the laboratory reference strains, strains obtained from repositories such as the ATCC or the NCTC, as well as strains studied in other laboratories. This collection of strains constitutes the positive controls which permit an assessment that the desired specific reactivity covers the spectrum of diversity within the taxon (ubiquitous specific reactivity). The list of strains constituting the collection of positive control strains is shown in Table 2.

In addition a set of negative controls must be carefully constituted. Ideally, negative controls will consist of at least a single strain, preferably of a number of strains of multiple species some of which being closely related to the target species and other being taxonomically distant therefrom. Preferably therefore, this collection should contain strains and species (taxa) which are representative of the clinical samples to be investigated. The negative control collection should permit an assessment of the specificity of the probe. The list of strains constituting the collection of negative control strains is shown in Table 3. As apparent from table 3, *Bacteroides forsythus*, *Porphyromonas gingivalis*, *Prevotella intermedia*, and *Prevotella nigrescens* were used as negative control. It is to be understood that, for example, *Porphyromonas gingivalis* was used as a negative control not against its own detection assays, but against the assays of the three other species, namely *Bacteroides forsythus*, *Prevotella intermedia*, and *Prevotella nigrescens*.

TABLE 2

Bacterial species and strains used as positive controls

| Species and strain designation | Clinical origin | Geographical origin |
|---|---|---|
| *Bacteroides forsythus* | | |
| ATCC 43037 | periodontal pocket | Boston, USA |
| 4019 M13 | periodontal pocket | Boston, USA |
| 4019 M21 | periodontal pocket | Boston, USA |
| 4019 M27 | periodontal pocket | Boston, USA |
| 4067 M7 | periodontal pocket | Boston, USA |
| 4090 M22 | periodontal pocket | Boston, USA |
| CR 141086 | periodontal pocket | Boston, USA |
| JL 142684 | periodontal pocket | Boston, USA |
| 2421 | periodontal pocket | Los Angeles, USA |
| 2344 | periodontal pocket | Los Angeles, USA |
| 2763 | periodontal pocket | Los Angeles, USA |
| *Porphyromonas gingivalis* | | |
| ATCC 33277 | periodontal pocket | Boston, USA |
| ATCC 49417 | periodontal pocket | Quebec, Canada |
| A7A1-28 | periodontal pocket | Arizona, USA |
| W50 | unknown | Bonn, Germany |
| W83 | unknown | Bonn, Germany |
| 16-1 | periodontal pocket | Tokyo, Japan |
| 17A1 | periodontal pocket | Quebec, Canada |
| E20-1 | endodontic infection | Buffalo, USA |
| 23A4 | periodontal pocket | Quebec, Canada |
| OMZ 409 | periodontal pocket | Zurich, Switzerland |
| HG 1020 | periodontal pocket | Buffalo, USA |
| HW 24D-5 | periodontal pocket | Quebec, Canada |
| OMZ 406 | periodontal pocket | Kenya |
| *Prevotella intermedia* | | |
| ATCC 25611 | empyema | New-York, USA |
| SUNYaB G8-9K-3 (ATCC 49046) | periodontal pocket | New-York, USA |
| A15/3 | endodontic abcess | Nijmegen, Netherlands |
| A9/3 | endontic abcess | Nijmegen, Netherlands |

TABLE 2-continued

Bacterial species and strains used as positive controls

| Species and strain designation | Clinical origin | Geographical origin |
|---|---|---|
| 89A | odontogenic abcess | Quebec, Canada |
| B192 | periodontal pocket | Nijmegen, Netherlands |
| BH20/30 | periodontal pocket | Winnipeg, Canada |
| MM22-8 | periodontal pocket | Quebec, Canada |
| NY 363 | periodontal pocket | Nijmegen, Netherlands |
| R22 | gingivitis | Rennes, France |
| MS/5B/367 | supragingival plaque | Winnipeg, Canada |
| SUNYaB 20-3 | subgingival plaque | New-York, USA |
| DNE | subgingival plaque | Quebec, Canada |
| *Prevotella nigrescens* | | |
| NCTC 9336 | Vincent's gingivitis | England |
| 5W2 | oral cavity | Quebec, Canada |
| BH 18/23 | periodontal pocket | Winnipeg, Canada |
| Cg 1265 | supragingival plaque | Winnipeg, Canada |
| MS/9b/918 | supragingival plaque | Winnipeg, Canada |
| R 102 | gingivitis | Rennes, France |
| S19g | localized juvenile | Rennes, France |

TABLE 3

Bacterial species and strains used as negative controls

| | |
|---|---|
| *Actinobacillus actinomycetemcomitans* | ATCC 29522 |
| *Bacteroides forsythus* | ATCC 43037 |
| *Bacteroides fragilis* | ATCC 25285 |
| *Bacteroides levli* | ATCC 29147 |
| *Bacteroides macacae* | ATCC 33141 |
| *Bacteroides merdae* | M-36 |
| *Bacteroides thetaiotaomicron* | ATCC 29741 |
| *Bacteroides vulgatus* | ATCC 8482 |
| *Campylobacter rectus* | ATCC 33238 |
| *Escherichia coli* | ATCC 33089 |
| *Fusobacterium nucleatum* | ATCC 10953 |
| *Porphyromonas asaccharolytica* | ATCC 25260 |
| *Porphyromonas circumdentaria* | 3325 |
| *Porphyromonas endodontalis* | ATTC35406 (H-370) |
| *Porphyromonas gingivalis* | ATCC 33277 |
| *Porphyromonas salivosa* | VPB 3313 |
| *Prevotella intermedia* | ATCC 25611 |
| *Prevotella nigrescens* | NCTC 9336 |
| *Prevotella oralis* | ATCC 33269 |
| *Prevotella oulora* | ATCC 43324 |
| *Pseudomonas aeruginosa* | ATCC 10145 |
| *Streptococcus mutans* | ATCC 33534 |
| *Streptococcus salivarius* | ATCC 25975 |

2. AP-PCR

The culture of bacteria was performed according to standard procedure for periodontal strains. Briefly, *P. gingivalis*, *P. intermedia* and *P. nigrescens* strains were grown to mid-log phase in Todd-Hewitt broth (BBL Microbiology Systems, Cockeysville, Md.) enriched with hemin (10 μg/ml) and vitamin K1 (1 μg/ml). Stock cultures were maintained by plating on the same medium containing 1.5% agar and 2% laked human blood. *B. forsythus* was grown in the same media further enriched with 10 mg/l of N-acetyl muramic acid. All cultures were incubated in an anaerobic chamber (80% N2, 10% H2 and 10% CO2; Coy Manufacturing Co., Ann Arbor, Mich.) at 37° C. All other bacteria used were grown using appropriate media and conditions known in the art.

Cells from broth cultures (5–8 ml) in the logarithmic phase were first harvested by centrifugation at 3,500× g for 20 min. The supernatant was discarded and individual cell pellets were stored at −20° C. Genomic DNA from all strains tested was obtained using a standard mini-prep procedure. Briefly, bacteria were lysed in 0.5% SDS and proteins removed by digestion with 100 µg/ml proteinase K. Cell wall debris, polysaccharides, and remaining proteins were removed by selective precipitation with CTAB, and high-molecular-weight DNA was recovered from the resulting supernatant by isopropanol precipitation after phenol/ chloroform/isoamyl and chloroform/isoamyl extractions. A8 final RNAse treatment of the pellet was then carried out to obtain bacterial genomic DNA. The concentration and quality of the genomic DNA were evaluated according to standard procedure (Sambrook, J. et al. (1989) *Molecular Cloning: A laboratory manual*, 2nd Ed., Cold Spring Harbor, N.Y.).

Optimization of amplification conditions

Since AP-PCR amplification conditions are likely to vary when using DNA from different species, optimization of these conditions must be carried out for each target species. For instance Triton X-100™ concentrations in the PCR buffer and annealing temperature are critical and thus, must be carefully determined for each target species. As an example the adequate conditions for AP-PCR amplification of *P. gingivalis* DNA is given below.

Amplification reactions were carried out in 25 µl volumes containing 200 µM each of dATP, dCTP, dGTP, and dTTP, 1.2 µM of selected primer, selection of which is described further, 25 ng of template DNA, and 2.5 units of Taq DNA polymerase (Pharmacia) in 1× PCR buffer (10 mM Tris-HCl, pH 9.0; 50 mM KCl, 1.5 mM MgCl2, 0.4% Triton X-100™ [vol/vol]). A negative control without template DAN was included in each experiment. The reaction mixtures were overlaid with mineral oil and subjected to amplification in a DNA Thermal Cycler™ (Perkin Elmer, Cetus) programmed to execute in sequence a pre-cycle, 30 amplification cycles and a post-cycle. The pre-cycle consists of a 5 minutes incubation at 94° C. Each amplification cycle consists of (I) a 60 seconds denaturation step at 94° C., (ii) a 90 seconds annealing step at 32° C. and (iii) a 120 seconds extention step at 72° C. The post-cycle consists of a 7 minutes final extention step at 72° C. The DNA thermal cycler was programmed to use the fastest available transition between each temperature. Upon completion of the PCR program, the samples were cooled to 4° C.

The optimal conditions for AP-PCR amplification for the three other species were similar except for a lower Triton X-100 concentration which was set at 0.1%.

Amplification products which constitute the random amplified polymorphic DNA (RAPD) fingerprints were compared by high resolution horizontal electrophoresis of 10 µl samples in 1.5% SeaKemGTG™ agarose gel (FMC, Rockland, USA) in Tris-acetate buffer (0.04M Tris-acetate, 0.002M EDTA, pH 8.5), stained with ethidium bromide, and photographed on a UV light transilluminator. DNA size markers (1 Kb or 100 bp DNA ladder, GIBCO BRL) were included in each gel.

Oligonucleotide screening to select the proper primer

A bank of 9- or 10-mer oligonucleotide of random sequence was screened to select the proper primer. The bank consists of approximately 100 different oligonucleotides originating from kits distributed by OPERON Technologies (10-mer primers) or synthesized with an Applied Biosystems model 394 synthesizer using phosphoramidite chemistry (9-mer primers). The latter primers were purified using the EasyPrep™ Oligo Prep Kit and the EasyPrep System™ (Pharmacia Biotech) according to the manufacturer's instructions.

A proper primer is defined as a primer which generates by AP-PCR, an amplicon which, in the RAPD fingerprints, is shared by all, if not the most, strains selected to encompass a large clinical and geographical diversity within the target species (ubiquity as specific reactivity). In addition, to being ubiquitously found in the targeted bacteria, the potentially specific marker, must be absent from each other strain but itself in the collection of negative controls including species that are taxonomically closely related to the target species (specificity).

The selected primers were as follows: OPA-01 for *B. forsythus*; 970-11 for *P. gingivalis*; OPA-13 for *P. intermedia* and for *P. nigrescens*.

Identification of a specific shared amplicon

Several amplicons shared by all studied strains of a target species can be generated and each is a potential candidate as a species-specific marker (in terms of size but not in terms of sequence) conditionally that it is absent from each strain in the set of negative controls. For instance, shared amplicons in the species *P. gingivalis* were observed at 815 bp with primer 910-09 and at 756 bp and 1155 bp with primer. As shown in FIG. 1, the amplicon shared by all strains of *B. forsythus* is visible at a location ca. 500 pb. This amplicon will be used as the species-specific anonymous probe to design a second generation probe specific for *B. forsythus*. The amplicons finally selected were as follows: 507 bp for *B. forsythus*; 1155 bp for *P. gingivalis*; 831 bp for *P. intermedia*; and ca. 1300 bp for *P. nigrescens*. Thus for example with *P. gingivalis*, out of the three possible specific amplicons only one was deemed to be satisfactory for further characterization.

Characterization of a specific marker

Once a candidate species-specific marker has been identified using the proper primer, quantities of the amplicon are needed for the following steps.

To generate a sufficient amount of working material, the AP-PCR products from four 25 µl amplifications of the type strain of each target species are loaded in a single well of a preparative minigel according to standard procedure (Sambrook, J. et al. (1989) *Molecular Cloning: A laboratory manual*, 2nd Ed., Cold Spring Harbor, N.Y.). The identified amplicon is executed from the agarose gel with a sterile razor blade on a UV transilluminator. The harvested gel portion is then sliced and DNA is purified using the Gene-Clean™ kit (BIO 101 Inc. La Jolla, Calif.) according to the manufacturer's instructions.

The purified DNA is then labeled by random priming with digoxigenin-dUTP (Boehringer Mannheim, Mannheim, Germany) according to the manufacturer's recommendations. It should be understood that other types of labeling are also contemplated within the scope of the present invention, since several methods can be typically used to detect the presence of hybrid polynucleotides. For example, the purified DNA can be labeled with a radioactive isotope (3H, 125I, 35S, 14C or 32P) and detected with autoradiography or the like. Other labels include, but are not limited to ligands which bind to antibodies labeled with fluorophores, chemiluminescent agents or enzymes. The choice of a particular isotope or ligand is dependent on numerous factors including stability, half life, the sensitivity required and inherent difficulties associated with a particular choice.

The choice of a particular label will in turn dictate the manner in which the label will be bound to the probe or primer (i.e. end-labeling, internal labeling and the like). Labeling can also occur by indirect means (as often found for non-isotopic labeling). For example, a ligand -anti-ligand system can be used. The anti-ligand can either be inherently detectable, or covalently bound to a detectable system (i.e. fluorophore, chemiluminescent compound). Ligands include antigenic substances, biotin and the like. Direct labeling of the probe or primer with horseradish peroxidase or alkaline phosphatase is also contemplated within the scope of the present invention. In addition, labels also include a variety of enzymes, as for example hydrolases, oxidoreductases, etc.

It should be understood that the detection of hybridization complexes can be assessed in a number of ways well-known in the art, which are dependent on the type of label used (i.e. validation detection, chemiluminescence, purification of the complexes by affinity).

Validation of the specificity of the anonymous probe

Each digoxigenin-labeled candidate of species-specific probe or anonymous DNA probe candidate, was validated by confirming its predicted specificity. This was performed by dot blot hybridization with homologous and foreign DNAs.

For dot blot hybridization, one µg of genomic DNA from each of the homologous and foreign species was heat denatured and spotted onto Hybond N™ nylon membranes (Amersham) before fixation by exposition to UV light. The nylon membrane was then prehybridized by a 2-hours incubation at 65° C. in the hybridization buffer containing 5× SSC (0.015M Na citrate, 0.15 NaCl, pH 7.0), 0.1% blocking reagent, 0.02% (w/vol) SDS and 0.1% (w/vol) sodium lauroylsarcosine. Single strands of the anonymous DNA probe candidate were prepared by boiling for 15 minutes 1 µg of the randomly labeled probe in 15 µl of buffer. The anonymous DNA probe candidate was then incubated with the nylon membrane in 10 ml of the hybridization buffer overnight at 65° C. under stringent conditions. Following hybridization, the blots were washed twice with 2× SSC, 0.1% SDS at room temperature for 15 minutes, and twice with 0.1× SSC, 0.1% SDS at 65° C. for 15 minutes. Carrying these procedures at 67° C. instead of 65° C., gave similar results with *B. forsythus*, *P. intermedia* and *P. nigrescens*.

A chemiluminescent detection was carried out in accordance with the manufacturer's protocol for the detection of DIG-labeled nucleic acids with Lumigen™ PPD [4-methoxy-4-(3-phosphate-phenyl)—spiro (1,2 dioxetane-3,2'-adamantane) disodium salt] (Boehringer). The membranes were exposed for 2 hours at room temperature to Kodak X-OMAT™ film.

This validation of potential species-specific probes is critical for the selection of the digoxigenin-labeled amplicon endowed with a restricted specificity for each target species. In several instances, shared amplicons identified in the previous steps had to be eliminated after they showed cross-hybridization with foreign species.

The digoxigenin-labeled 507 bp amplicon identified in *B. forsythus* was positive by hybridization with the 10 *B. forsythus* strains tested and negative with the 22 taxonomically related and unrelated species (FIG. 2). The digoxigenin-labeled 1155 bp amplicon identified in *P. gingivalis* was positive by hybridization with the 17 *P. gingivalis* strains tested and negative with 18 strains of taxonomically related and unrelated species. The digoxigenin-labeled 831 bp amplicon identified in *P. intermedia* was positive by hybridization with the 13 *P. intermedia* strains tested and negative with 27 strains of 21 taxonomically related and unrelated species including 7 strains of *P. nigrescens*). Similarly, the digoxigenin-labeled ca. 1300 bp amplicon identified in *P. nigrescens* was positive by hybridization with the 7 *P. nigrescens* strains tested and negative with 33 strains of 21 taxonomically related and unrelated species including 13 strains of *P. intermedia*.

This work therefore, has established that the polymerase chain reaction using arbitrary primer can be used to design and construct DNA probes, referred to as anonymous probes (since no sequence or genetic data was known prior to the obtention of the probe) specific for a variety of bacterial species. Four such anonymous probes are described here: a digoxigenin-labeled 507 bp probe generated by AP-PCR using primer OPA-01, specific for *B. forsythus*; a digoxigenin-labeled 1146 bp probe generated by AP-PCR using primer 970-11, specific for *P. gingivalis*; a digoxigenin-labeled 831 bp probe generated by AP-PCR using primer OPA-13, specific for *P. intermedia*; a digoxigenin-labeled ca. 1300 bp probe generated by AP-PCR using primer OPA-13, specific for *P. nigrescens*.

DERIVATION OF SECOND GENERATION PROBE

Under certain clinical circumstances, wherein the sensitivity of the assay must be increased, it may appear desirable to enhance the detection capability of the diagnostic system by using a step of amplification of the DNA of the target species. In a second embodiment of the present invention, the sequence of each validated anonymous probe is determined and used to select a primer pair which can then be used for PCR amplification. Each selected primer pair will serve two roles: first, to synthesize a DNA fragment internal to the anonymous probe sequence, which, after labelling, will be used as a second generation probe; and second, to amplify a specific sequence in the genomic DNA of target species in clinical specimens. The latter amplification product will finally be detected by hybridization with the second generation probe specific for the target species. Details of specific anonymous probes and their second generation probe derivatives is found in Table 4.

TABLE 4

| | Specifications of primers and probes | | | |
|---|---|---|---|---|
| | B. forsythus | P. gingivalis | P. intermedia | P. migrescens |
| Sequence of AP-PCR primer | 5' CAGGCCCTTC 3'[1] (SEQ ID NO:1) | 5' GTAAGGCCG 3' (SEQ ID NO:2) | 5' CAGCACCCAC 3' (SEQ ID NO:3) | 5' CAGCACCCAC 3' (SEQ ID NO:3) |
| Size (bp) of anonymous probe | 507 | 1155 | 831 | ca. 1300 |
| Specific PCR primer pairs | | | | |
| 5' sequence | 5' ATGCTCCTGCTGGGT-CTGTT 3'(SEQ ID NO:4) | 5' AATCGTAACGGGCGA-CACAC 3'(SEQ ID NO:6) | 5' CAGCACCCACAACGA-TATGA 3'(SEQ ID NO:8) | 5' TTATGTTACCCGTTA-TGATGGAAG 3' (SEQ ID NO:10) |

TABLE 4-continued

Specifications of primers and probes

| | B. forsythus | P. gingivalis | P. intermedia | P. nigrescens |
|---|---|---|---|---|
| 3' sequence | 5' CGACACTTCGGATCG-TTTAG 3'(SEQ ID NO:5) | 5' GGGTTGCTCCTTCAT-CACAC 3'(SEQ ID NO:7) | 5' TTCCATCTTCTCTGC-CTGTC 3'(SEQ ID NO:9) | 5' ATGGCGAAATAGGA-ATGAAAGTTA 3' (SEQ ID NO:11) |
| size | 20-mer | 20-mer | 20-mer | 24-mer |
| Size of 2nd generation probe | 392 bp | 593 bp | 754 bp | ca. 1100 bp |

Preparative AP-PCR

In order to prepare a sufficient amount of working material, the AP-PCR product of the type strain of each target species was loaded in a preparative minigel and the identified amplicon was excised therefrom and purified as described above.

Cloning and sequencing of the anonymous probe

Cloning and sequencing of the anonymous probes was carried out according to well known methods. Briefly, the amplified fragment excised from preparative agarose gels was ligated into the linearized TA Cloning Vector (Invitrogen) according to the manufacturer recommendations. Plasmid DNA was extracted by using a Magic-miniprep kit™ (Promega) according to the manufacturer instructions and the identity of the cloned AP-PCR product was verified by restriction digestion with EcoR1 and separation of the resulting fragments on agarose gels using standard procedures (Sambrook, J. et al. (1989) *Molecular Cloning: A laboratory manual*, 2nd Ed., Cold Spring Harbor, N.Y.). The GlassMAX™ DNA Isolation Spin Cartridge System (GIBCO BRL) was used to purify the recombinant plasmid according to the manufacturer instructions. Sequencing of the cloned fragment was done by the dideoxy-chain termination method using universal primers (Sequenase™ kit, USB) and following standard procedures. The nucleotide sequence of the anonymous probes specific for *B. forsythus, P. gingivalis* and *P. intermedia* is shown in FIGS. 3, 4 and 5, respectively. The sequence of the *P. nigrescens* species-specific marker was obtained as two small stretches, 292 and 300 bp, respectively, (FIG. 6) at each end of the ca. 1300 bp cloned fragment.

Selection of a primer pair

The exact sequence obtained can now be used to select the optimal primer pair to be used in a PCR amplification. Optimal upstream and downstream sequences for PCR amplification can be predicted with the help of the OLIGO™ Primer Analysis Software (National Biosciences, Inc.). For instance, in the case of *P. intermedia*, six oligonucleotide sequences to constitute four primer-pairs were synthesized. The primer pairs were predicted to amplify a fragment internal to the 831 bp sequence of *P. intermedia*. However, of these four primer pairs, only one yielded an amplification product that met the following criteria: 1) it is unique and of the expected size; 2) it is present in strains of the target species and absent in the collection of negative controls; 3) it is present in all strains tested of the target species; and 4) it gives a good amplification yield. The four *P. intermedia* primer-pairs tested were as follows: primer pair #1, upper primer, 22 mer, 5' AGTCCTTCGC TTTCTTGCTT AC 3' (SEQ ID NO:12), lower primer, 22 mer, 5' GAGTTCCTGC TTTTGTCTTT CA 3' (SEQ ID NO:13), amplification product: 251 bp; primer pair #2, upper primer, 22 mer, 5' AGTCCTTCGC TTTCTTGCTT AC 3' (SEQ ID NO:12), lower primer, 22 mer, 5' ATTTCCATCT TCTCTGCCTG TC 3' (SEQ ID NO:14), amplification product: 386 bp; primer pair #3, upper primer, 20 mer, 5' CAGCACCCAC AACGATATGA 3' (SEQ ID NO:8), lower primer, 20 mer, 5' AAGCAAGAAA GCGAAGGACT 3' (SEQ ID NO:15), amplification product: 390 bp; and primer pair #4, upper primer, 20 mer, 5' CAGCACCCAC AACGATATGA 3' (SEQ ID NO:8), lower primer, 20 mer, 5' TTCCATCTTC TCTGCCTGTC 3' (SEQ ID NO:9), amplification product: 754 bp.

Only primer pair #4 yielded a product that satisfied the 4 criteria mentioned above.

Oligonucleotide synthesis

The oligonucleotides to be used for PCR priming were synthesized according to known methods with an Applied Biosystems model 394 synthesizer using phosphoramidite chemistry. The primers were purified using the EasyPrep Oligo Prep™ kit and the EasyPrep System™ (Pharmacia Biotech) according to the manufacturer's instructions.

1—Determination of the Optimal PCR Conditions

For each target species, and for each potential suitable primer pair identified, the optimal annealing temperature, which is critical in the PCR conditions, must be determined. The optimal thermal stringency is usually obtained with the highest annealing temperature which allows the synthesis of the desired amplification product that meets the four criteria mentioned above. A series of experiments were performed in which annealing temperatures were adjusted degree by degree within a range that extends from –5° C. to +15° C. from the temperature predicted with the help of the OLIGO™ software.

All PCR reactions were performed in a reaction mixture containing 1× PCR buffer (10 mM Tris-HCl [pH 9], 50 mM KCl, 1.5 mM MgCl2, 0.1% Triton X-100, 200 µM of each of the 4 dNTPs, 50 pmol of each primer, 2.5 U of Taq DNA polymerase (Cetus, Emeryville, Calif.), and 50 ng of genomic DNA in a final volume of 50 µl. The reaction mixture was overlaid with a drop of mineral oil and incubated in a programmable DNA thermal cycler (Perkin-Elmer Cetus). One negative control (absence of template DNA) was performed for each set of amplification.

PCR conditions specific for *B. forsythus*

PCR conditions for *B. forsythus* were programmed to execute in sequence a pre-cycle and 30 amplification cycles. The pre-cycle consists of a 5 minutes incubation at 94° C. Each amplification cycle consists of (I) a 60 seconds denaturation step at 94° C., (ii) a 45 seconds annealing step at 65° C. and (iii) a 30 seconds extention step at 72° C. Specific primers for amplification of an internal sequence, Bf 392-1 (20-mer) 5' ATGCTCCTGC TGGGTCTGTT 3' (SEQ ID NO:4), and Bf 392-2 (20-mer) 5' CGACACTTCG GATCGTTTAG 3' (SEQ ID NO:5) were used. The sequence of the target internal sequence of 392 bp was shown to be:

```
ATGCTCCTGC TGGGTCTGTT TGAGGTATTC GATACCGTAA TCGTGCTGCG CTTTAGTCCA   60
TGCAACGACT TCGGGATTTT CCTTATCTTC GAGCCAGCGG AACGGATCGG TGATCACCAC  120
GTTATGCAAC GTATCTTTTA CGGGTTTTTG AAGAGTCACC GGGGGGCGAA ACGCTACTTG  180
AGCGTAAGAG GTCACTGTCA TGGTCAAAGT AAGTGGAAAC ATGAAAAAAT TCTTCATCTN  240
CAATTGTATT TTTGAATAAG TTTGTTTTTG TGTNCAAACA TAGATAAAAA AGCTGAGATT  300
AAATATGGAA AAGAAGATAA ATCTCGGACG CGGTTTTTCT TTTTCGGAGA AAATGATGTA  360
CCTTTGCATT TGCTAAACGA TCCGAAGTGT CG                                392
```
(SEQ ID NO: 16).

PCR conditions specific for *P. gingivalis*

PCR conditions for *P. gingivalis* were programmed to execute in sequence a pre-cycle and 30 amplification cycles. The pre-cycle consists of a 5 minutes incubation at 94° C. Each amplification cycle consists of (I) a 60 seconds denaturation step at 94° C., (ii) a 60 seconds annealing step at 70° C. and (iii) a 30 seconds extention step at 72° C. Specific primers for amplification of an internal sequence, Pg 593-1 (20-mer) 5' AATCGTAACG GGCGACACAC 3' (SEQ ID NO:6) and Pg 593-2 (20-mer) 5' GGGTTGCTCC TTCATCACAC 3' (SEQ ID NO:7) were used. The sequence of the target internal sequence of 593 pb was shown to be:

PCR conditions for *P. intermedia* were programmed to execute in sequence a pre-cycle and 30 amplification cycles. The pre-cycle consists of a 5 minutes incubation at 94° C. Each amplification cycle consists of (I) a 60 seconds denaturation step at 94° C., (ii) a 45 seconds annealing step at 65° C. and (iii) a 30 seconds extention step at 72° C. Specific primers for amplification of an internal sequence, Pi 754-1 (20-mer) 5' CAGCACCCAC AACGATATGA 3' (SEQ ID NO:8) and Pi 754-2 (20-mer) 5' TTCCATCTTC TCTGCCTGTC 3' (SEQ ID NO:9) were used. The sequence of the target internal sequence of 754 bp was shown to be:

```
AATCGTAACG GGCGACACAC CGGGTACCGC CCGGAGATCG GCCGCCAAAT AGGACTGTGG   60
GACGAAAGCT GTACGGAGCG GAATATGATC ACCGGTTCGG ATTTCGCAGC CCTCACCGAC  120
GAGGAACTGC GCCCTCGGAT AGGCGAACTG CGTATCATGT CCGCGCTCGT CGATGGACAA  180
GGAAAGGCTT GTACGCCTGC TGCAGGAAGG CTCGCGAAGG TGGTGGCCGT GACGGGCGAC  240
GGCACGAACG ACGCTCCTGC ACTCAACCGC GCACAGGTGG GCCTCTCGAT GGGCGATGGC  300
ACTGCGTAGC CAAAGAGGCG AGCGACATCA CCATTCTGGA CAATTCTTTC AGCAGCATTG  360
CCAAAGCCGT TATGTGGGGA CGATCGCTTT ATCGGAATAT CCGCCGTTTT ATCCTCTTTC  420
AGATGACCAT CAACGTCGTG GCCTGTATCA TCGTTCTGAT CGGCGCATTT GTGGGTACGG  480
AGTCGCCCCT TACCGTGACG CAAATGCTGT GGGTCAATCT CATCATCGAC ACTTTCGCCG  540
CCTTGTCCTT GGCTTCGCTC CCTCCCGACA AGGGTGTGAT GAAGGAGCAA CCC          593
```
(SEQ ID NO: 17).

PCR conditions specific for *P. intermedia*

```
              CAGCACCCAC AACGATATGA TCTGCCACAG CTTTTGAACC ATTATGTTCA GCACTTACAC   60
              TTGCCAACAA CATTATATCG TCCCATGGCA AATAGCCAAC TTTTGNCTCA AGCCCGATAT  120
              TGAACTTATC GTGCCCGTTA TAGTGCAAGT CAAGACCTGT CAAAGAAGCT CCAAGGTAGC  180
              CTTTACCCTC TTGAAACTGT GCATGAATAC CTAATGATAA TGTTAATCCT AATAAAAGGA  240
              GGGATAATTT CTTCATCATA ATAATACTGT TATTGTAAAA TCTATTTATT GCTAAATTCC  300
              ATTGACAAAG GTAGTAGAAA TATTTGAATT ACAAAAATTA TTGCCTATCT TTGTGCCTGA  360
              TTTGCAAATA AGTCCTTCGC TTTCTTGCTT ACAAATATGC TTTAAAACGT ATGAATAAAA  420
              AATTAATTAC ACTGATATTA CTAAGCTGTC TTCACGATAA ATTGTTTTGC ACAAACGGGC  480
              GAAATATTTA TAAATTGGGA TACAAAACCT TTCAAGAAAC GTGAAACCCG TGCTGTTTGG  540
              CTAACTACTT TGAACAATCT TGACTGGCCA AAGACATTTG CAAACTCGGA GNGAGGTATT  600
              GAAAGACAAA AGCAGGAACT CATTGATATT TTAGATAAAT ATGTCGCTGC AAACATTAAT  660
              ACCGTTCTGT TGCAAACGCG TGTGCGTGCA GCCACCATTT ATCCGTCCAA CATAGAACCT  720
```

-continued

TGGGACAAAT GCTTGACAGG CAGAGAAGAT GGAA          754

(SEQ ID NO: 18).

PCR conditions specific for *P. nigrescens*

PCR conditions for *P. nigrescens* were programmed to execute in sequence a pre-cycle and 30 amplification cycles. The pre-cycle consists of a 5 minutes incubation at 94° C. Each amplification cycle consists of (i) a 60 seconds denaturation step at 94° C., (ii) a 45 seconds annealing step at 65° C. and (iii) a 30 seconds extention step at 72° C. Specific primers for amplification of an internal sequence, Pn1100-1, a 24-mer having the sequence 5' TTATGTTACC CGTTAT-GATG GAAG 3' (SEQ ID NO:10) in position 44 of the 5' end and Pn 1100-2, a 24-mer having the sequence 5' ATG-GCGAAAT AGGAATGAAA GTTA 3' (SEQ ID NO:11) in estimated position 1067 of the 3' end. The sequence of the target internal sequence of ca. 1100 bp was shown to be:

*forsythus*, a single band at 392 bp is observed in 11 strains of *B. forsythus* while no band is observed in the 22 strains from 22 taxonomically related and unrelated species were observed.

With *P. gingivalis*, a single band at 593 bp is observed in 10 strains of *P. gingivalis* while no band is observed in 8 strains from 8 taxonomically related and unrelated species.

With *P. intermedia*, a single band at 754 bp is observed in 13 strains of *P. intermedia* while no band is observed in 27 strains from 21 taxonomically related and unrelated species including 7 strains of *P. nigrescens*.

With *P. nigrescens*, a double band is observed at ca. 1100 bp in 7 *P. nigrescens* strains while no band is observed in 33 strains from 21 taxonomically related and unrelated species including 13 strains of *P. intermedia*.

TTATGTTACC CGTTATGATG GAAGTAGTTG GGCGTTGTGT TGCTATAATC ATGTGAATGC  60

CTACCGCACG CGCCAGCTGG GCGATACGGG TGATAGGCAT TTCAATTTCT TTTCCAGCGG  120

TAAGGATAAG GTCTCCGAAC TCATCAATGA TGACAACGAT GTACGGTATG AACTCGTGTC  180

CTCCCGCAGG ACTAAGCTGA TGGCTAAGGA ACTTCTTGTT ATACTCTTTT ATATTGCGCG  240

CTCCTGTAG                                                        249

(SEQ ID NO: 19) separated of about 700 bp from:

AAATTAAGGG TTGGATACTN CCAATTGGGG AAAGGTTCGT GTGGATTAAT AGGTGTTNCA  60

AGGTCTGTCG TGCCTGCCAC CCCCTTACCT TGTGCCTTTT CCAACCCGAC AGGGACATTA  120

ACTTTCATTC CTATTTCGCC AAT                                         142

(SEQ ID NO: 20).

PCR synthesis of selected internal sequences and labeling thereof

For the construction of each nonisotopic second generation probe, synthesis of the internal sequence flanked by the selected primer pair was achieved by amplification of the genomic DNA of the reference type strain of each target species. Thus the following strains were used: *B. forsythus* ATCC 43037, *P. gingivalis* ATCC 33277, *P. intermedia* ATCC 25611 and *P. nigrescens* NTCC 9336.

The amplified DNA in 5 µl aliquots was then labeled by random priming with digoxigenin-dUTP (Boehringer Mannheim), according to the manufacturer's recommendations.

2—Validation of the Specificity of the Second Generation Probes

A further validation is performed to provide additional evidence as to the specificity of the method of detection of bacteria associated with periodontal disease, and of the primers and probes directed against these bacteria.

Gel electrophoresis analysis

To verify that each amplification product yields a single fragment of the expected size, and is present only in the genomic DNA of the strains homologous to the target species and is absent in the genomic DNA of foreign species gel electrophoresis analysis was performed.

For this purpose, 10 µl aliquots of amplified DNA were resolved in 1.5% agarose gel (SeaKem™ GTG) in 0.04M Tris-acetate, 0.002M EDTA, pH 6.5, stained with ethidium bromide, and photographed on a UV transilluminator. The results obtained were as follows: As shown in FIG. 7 for *B.*

Confirmation of the specificity by dot blot hybridization

To verify that the amplification product of the strains homologous to the target species hybridizes with the labeled second generation DNA probe, dot blot hybridization was performed. Dot blot hybridization also allows a verification that the second generation DNA probe does not react with the PCR reaction mixture from foreign species.

For dot blot hybridization, aliquots of alkaline-denatured amplified product from each of the homologous and foreign species were spotted onto Hybond N™ nylon membranes before fixation by exposition to UV light for five min. The nylon membrane was then processed in a prehybridization step by incubation for 2 hours at 65° C. in the hybridization buffer containing 5× SSC (0.015M Na citrate, 0.15 NaCl, pH 7.0), 0.1% blocking reagent, 0.02% (w/vol) SDS and 0.1% (w/vol) sodium lauroylsarcosine. Single strands of the labeled second generation DNA probe are prepared by heat-denaturation by boiling for 15 minutes 1 µg of the randomly labeled probe in 15 µl of buffer. This volume of second generation DNA probe were then incubated with the nylon membrane in 10 ml of the same buffer for overnight hybridization under stringent conditions at 65° C. After hybridization, the blots are washed twice with 2× SSC, 0.1% SDS at room temperature for 15 minutes, and twice with 0.1× SSC, 0.1% SDS at hybridization temperature (65° C.) for 15 minutes.

A chemiluminescent detection was carried out in accordance with the manufacturer's protocol for the detection of DIG-labeled nucleic acids with Lumigen™ PPD [4-methoxy-4-(3-phosphate-phenyl)—spiro (1,2 dioxetane-3,2'-adamantane) disodium salt] (Boehringer). The membranes are exposed from 15 to 60 min at room temperature to Kodak X-OMAT™ film. As shown in FIG. 8, the dot blot hybridization using the *B. forsythus* labeled second generation probe gave positive results with 11 strains of *B. forsythus* and negative results with 22 strains of taxonomically related and unrelated species. Using the *P. gingivalis* probe, decoration was observed with the 14 strains of *P. gingivalis*, while no hybridization signal was observed with 10 strains of taxonomically related and unrelated species. The *P. intermedia* probe yielded a positive signal with all 13 strains of *P. intermedia* but no signal with 27 strains of 21 taxonomically related and unrelated species including 7 strains of *P. nigrescens*. The *P. nigrescens* probe yielded a positive signal with all 7 strains of *P. nigrescens* but no signal with 33 strains from 21 taxonomically related and unrelated species including 13 strains of *P. intermedia*.

CONCENTRATION OF THE TARGET FROM THE SAMPLE

In order to further increase the sensitivity of the detection of bacteria associated with periodontal disease, a chosen species or type of such bacteria can be concentrated form the initial sample from the patient. Immunomagnetic particle-based separation can be used efficiently to separate and isolate specific cells from a heterologous cell suspension (Olsvik et al. 1994, *Clinical Microbiology Reviews* 7:43–54). Bacteria are specifically separated from the specimen, resulting in a useful sample for PCR with little or no nonspecific DNA or interfering factors.

Another procedure aiming at the specific capture of target DNA in mixed samples prior to amplification, thereby concentrating the target sequence and removing irrelevant DNAs and other potential inhibitors of PCR, is a contemplated alternative. The capture per se includes two successive steps: (i) a step of liquid-phase hybridization of the biotinylated oligonucleotide probe to the target DNA and (ii) a step of capture of the duplex "target DNA-biotinylated oligonucleotide" using streptavidin-coated paramagnetic beads. Thereafter, following appropriate washes, the target DNA bound to streptavidin-coated beads is subjected to a PCR-DNA probe assay for accurate detection.

There are three major advantages in using DNA capture prior to PCR: (i) an increase in sensitivity (concentration of the target sequence before amplification); (ii) an increase in specificity (hybridization to the oligonucleotide capture sequence), and (iii) no need to preserve cellular integrity as is necessary in the immunomagnetic procedure to capture bacterial cells.

EXAMPLE 1

Immunomagnetic Capture and PCR-DNA Detection Probe of *Porphyromonas gingivalis*

Coating of immunomagnetic beads (IMBs)

Immunomagnetic beads (IMBs: Dynabeads M-280, 2.8 μm in diameter, 5×10⁸ beads per ml) are uniform superparamagnetic polystyrene beads with covalently linked sheep anti-mouse immunoglobulin G (Dynal ALS, Oslo, Norway). The beads were washed twice with PBS-bovine serum albumin (0.1%) (PBS-BSA), separated by magnetic force, and then resuspended to the original volume in PBS-BSA. Thereafter, they were coated with capture monoclonal antibody (MAb) by incubation in a 1:50 dilution of the antibody for 24 h at 4° C. with rotation (50 rpm) to avoid settling of the IMBs. The MAb (immunoglobulin G1-subclass) used was a culture supernatant of hybridoma 1C4 specific for the hemagglutinating adhesin HA-Ag2 of *P. gingivalis* ATCC 33277. The amount of antibody required to achieve optimal binding of the target bacteria was determined in a series of pilot experiments; the highest number of bound bacteria was obtained with 50 μg of immunoglobulin G per mg of immunomagnetic beads. The coated IMBs were stored and washed before use as described by the manufacturer.

Immunomagnetic isolation procedure

A 15-μl volume of MAb-coated Dynabeads was mixed with 1 ml of each dilution of the bacterial suspension, and the mixture was incubated at 4° C. with continuous shaking for 30 min. The beads with the attached bacteria were washed three times in 1 ml of PBS-BSA with the aid of magnetic separation and were finally suspended in 30 μl of deionized water. For the recovery of genomic DNA, the beads and their attached bacteria were heated at 95° C. for 10 min and were briefly centrifuged, and 5 μl of the supernatant was used in the PCR.

Immunomagnetic PCR (IM-PCR) detection of *P. gingivalis* in spiked mixed bacterial suspensions A series of three experiments was used to assess the ability of the IM-PCR procedure and then detection of the amplification product by dot blot hybridization to specifically detect *P. gingivalis*. In the first experiment a serial dilution of *P. gingivalis* ATCC 33277 in PBS was used to obtain bacterial concentrations ranging from 10⁷ bacteria to 1 bacterium per ml. In the second experiment aliquots of a mixed suspension of seven oral species were prepared so that the final total concentration of each species in each aliquot was 10⁶ bacteria per ml. The selected species were the five gram-negative bacteria *Fusobacterium nucleatum* ATCC 10953, *Porphyromonas salivosa* 3313, *Prevotella intermedia* ATCC 25611, *Prevotella nigrescens* NCTC 9336 and *Wolinella recta* ATCC 33238 and the two gram-positive bacteria *Actinomyces naeslundii* WVU 627 and *Streptococcus mutans* ATCC 25175. The aliquots were spiked with *P. gingivalis* ATCC 33277 serially diluted from 10⁷ bacteria to 1 bacterium per ml. With this dilution scheme, the concentration of the spiked bacteria decreased while the concentration of the other bacteria remained the same. Finally, a pool of submarginal plaque samples obtained from three periodontally healthy subjects was constituted by resuspending approximately 5 mg of plaque in 10 ml of reduced transport fluid. Anaerobically culturing of an aliquot of the pooled plaque sample revealed that it was negative for *P. gingivalis*. Aliquots of the pooled plaque sample were spiked with *P. gingivalis* ATCC 33277 serially diluted from 10⁷ bacteria to 1 bacterium per ml and subjected to the IM-PCR and dot blot hybridization procedure. All experiments were conducted in triplicate.

Detection of *P. gingivalis* in spiked mixed bacterial suspensions

The sensitivity of the IM-PCR/DNA probe procedure for detecting specific bacteria was first investigated with serial dilutions of *P. gingivalis* in PBS. The immunomagnetically isolated cells were subjected to PCR, and the amplified products were detected by dot blot hybridization with the 593-bp probe. The lowest concentration of *P. gingivalis* that gave a positive signal was 10² cells per ml, i.e., approximately 16 bacteria in the assay. In aliquots containing a mixture of 7×10⁶ heterologous bacteria spiked with a serial dilution of *P. gingivalis*, the same sensitivity was obtained. The same threshold of sensitivity was also obtained by using IMS-isolated cells from a pooled *P. gingivalis*-negative plaque sample spiked with a serial dilution of *P. gingivalis*.

Detection of *P. gingivalis* in clinical samples

To assess the potential usefulness of the IM-PCR/DNA probe procedure for laboratory diagnosis, we examined its performance with 19 clinical samples. The dispersed subgingival plaque samples were subjected to immunomagnetic separation, and cell lysates amplified by PCR were detected with the 593-bp probe. The seven samples which were culture positive for *P. gingivalis* were identified by the IM-PCR/DNA probe procedure. In addition, four samples that were *P. gingivalis* negative by culture were identified as positive by IM-PCR and dot hybridization. The results derived from the 19 clinical samples assayed either by the IM-PCR/DNA probe procedure or by culture are summarized in Table 5.

TABLE 5

Frequency distribution of results by the IM-PCR/DNA probe procedure or culture for the detection of detect *P. gingivalis* in 19 clinical samples

| | No. of samples | | | |
|---|---|---|---|---|
| Sample site or disease | Culture positive | Culture negative | IM-PCR/ DNA probe positive | IM-PCR/ DNA probe negative |
| Healthy gingiva, 7 sites in 7 patients | 0 | 7 | 1 | 6 |
| Gingivitis, 3 sites in 3 patients | 1 | 2 | 1 | 2 |
| Periodontitis, 9 sites in 3 patients | 6 | 3 | 9 | 0 |

As the above results demonstrate, the present invention provides a rapid, specific and sensitive method for detecting bacteria associated with periodontal disease in a sample, as exemplified above with *P. gingivalis*. The method according to present invention permits to detect as little 100 *P. gingivalis* cells in a sample containing 7×106 diverse nontarget bacteria, which was sufficient to yield a positive signal following PCR amplification and detection with a DNA probe.

While the invention has been described with particular reference to the illustrated embodiment, it will be understood that numerous modifications thereto will appear to those skilled in the art. Accordingly, the above description and accompanying drawings should be taken as illustrative of the invention and not in a limiting sense.

---

We claim:

1. A probe for the specific detection and identification of *Bacteroides forsythus*, which comprises a nucleic acid sequence from *Bacteroides forsythus* of about 507 bp, wherein said probe is obtained by amplification of *Bacteroides forsythus* strain ATCC 43037 nucleic acid with primer OPA-01 as set forth in SEQ ID NO:1.

2. A probe for the specific detection and identification of *Porphyromonas gingivalis*, which comprises a nucleic acid sequence from *Porphyromonas gingivalis* of about 1155 bp, wherein said probe is obtained by amplification of *Porphyromonas gingivalis* strain ATCC 33277 nucleic acid with primer 970-11 as set forth in SEQ ID NO:2.

3. A probe for the specific detection and identification of *Prevotella intermedia*, which comprises a nucleic acid sequence from *Prevotella intermedia* of about 831 bp, wherein said probe is obtained by amplification of *Prevotella intermedia* strain ATCC 25611 nucleic acid with primer OPA-13 as set forth in SEQ ID NO:3.

4. A probe for the specific detection and identification of *Prevotella nigrescens*, which comprises a nucleic acid sequence from *Prevotella nigrescens* having an apparent size of about 1300 bp, as estimated by agarose gel electrophoresis, wherein said probe is obtained by amplification of *Prevotella nigrescens* strain NCTC 9336 nucleic acid with primer OPA-13 as set forth in SEQ ID NO:3.

5. A composition of polynucleotide probes for the detection of bacteria associated with periodontal disease, wherein said probes are obtained from amplification of nucleic acid sequences from bacteria selected from the group consisting of *Bacteroides forsythus* strain ATCC 43037, *Porphyromonas gingivalis* strain ATCC 33277, *Prevotella intermedia* strain ATCC 25611 and *Prevotella nigrescens* strain NCTC 9336, with primers selected from the group consisting of primers as set forth in SEQ ID NO:1, SEQ ID NO:2 and SEQ ID NO:3, and wherein said probes are capable of selectively hybridizing, under stringent hybridizing conditions with the nucleic acid sequences from said bacteria associated with periodontal disease.

6. A primer pair for the detection of bacteria associated with periodontal disease, wherein said primer pair is derived from a probe comprising a nucleic acid sequence from said bacteria, wherein said probe is obtained from amplification of a nucleic acid sequence of a bacteria selected from the group consisting of *Bacteroides forsythus* strain ATCC 43047, *Porphyromonas gingivalis* strain ATCC 33277, *Prevotella intermedia* strain ATCC 25611 and *Prevotella nigrescens* strain NCTC 9336 with a primer selected from the group consisting of primers as set forth in SEQ ID NO:1, SEQ ID NO:2 and SEQ ID NO:3, and wherein said primer pair is being used for amplification of a nucleic acid specific for a particular bacteria associated with periodontal disease, under PCR conditions.

7. A primer pair according to claim 6, wherein said primer pair is selected from the group consisting of primer pairs as set forth in SEQ ID NO:4 and SEQ ID NO:5, SEQ ID NO:6 and SEQ ID NO:7; SEQ ID NO:8 and SEQ ID NO:9, and SEQ ID NO:10 and SEQ ID NO:11.

8. A method of detecting in a sample obtained from the mouth of a human patient, bacteria associated with periodontal disease, said method comprising the steps of:

contacting the bacteria present in said sample with at least one probe specific for a bacteria associated with periodontal disease, under conditions that will release the nucleic acid therefrom and that will permit a selective hybridization of said nucleic acid with said probe, wherein said probe is obtained from amplification of a nucleic acid sequence of a bacteria selected from the group consisting of *Bacteroides forsythus* strain ATCC 43037, *Porphyromonas gingivalis*, strain ATCC 33277, *Prevotella intermedia* strain ATCC 25611 and *Prevotella nigrescens* strain NCTC 9336 with a primer selected from the group consisting of primers as set forth in SEQ ID NO:1, SEQ ID NO:2 and SEQ ID NO:3; and detecting hybridization of the probe with the nucleic acid of said bacteria as an indication of the presence of the bacteria in the sample.

9. The method of claim 8, wherein at least one specific species or type of bacteria associated with periodontal disease is immuno-captured prior to the contacting thereof with said probe.

10. A method of detecting in a sample obtained from the mouth of a human patient, bacteria associated with periodontal disease, said method comprising the steps of:

contacting the bacteria present in said sample with a primer pair derived from the sequence of a probe specific for bacteria associated with periodontal disease, under conditions that will release the nucleic acid therefrom and that will permit a selective hybridization of said nucleic acid with said primer pair, wherein said probe is obtained from amplification of a nucleic acid sequence of a bacteria selected from the group consisting of *Bacteroides forsythus* strain ATCC 43037, *Porphyromonas gingivalis* strain ATCC 33277, *Prevotella intermedia* strain ATCC 25611 and *Prevotella nigrescens* strain NCTC 9336 with a primer selected from the group consisting of primers as set forth in SEQ ID NO:1, SEQ ID NO:2 and SEQ ID NO:3;

amplifying said nucleic acid using PCR technology; and detecting the amplified PCR product characteristic of a specific bacteria associated with periodontal disease.

11. A method according to claim 10, wherein the primer pair derived from the sequence of the probe is selected from the group consisting of primer pairs as set forth in SEQ ID NO:4 and SEQ ID NO:5, SEQ ID NO:6 and SEQ ID NO:7; SEQ ID NO:8 and SEQ ID NO:9; and SEQ ID NO:10 and SEQ ID NO:11.

12. The method of claim 10, wherein at least one specific species or type of bacteria associated with periodontal disease is immuno-captured prior to the contacting thereof with said primer pair.

13. A diagnostic kit for use in determining the presence of a specific polynucleotide sequence of a bacteria associated with periodontal disease, which comprises in a container a synthetic oligonucleotide probe comprising a nucleic acid sequence of a bacteria selected from the group consisting of *Bacteroides forsythus* strain ATCC 43047, *Porphyromonas gingivalis* strain ATCC 33277, *Prevotella intermedia* strain ATCC 25611 and *Prevotella nigrescens* strain NCTC 9336, complementary to the specific polynucleotide sequence or portion thereof;

wherein said synthetic oligonucleotide probe is obtained from amplification of the nucleic acid sequence of said bacteria with a primer selected from the group consisting of primers as set forth in SEQ ID NO:1, SEQ ID NO:2 and SEQ ID NO:3.

14. A diagnostic kit for use in determining the presence of a specific polynucleotide sequence of a bacteria associated with periodontal disease, which comprises in a container synthetic oligonucleotide primer pair derived from the sequence of a probe specific for bacteria associated with periodontal disease, said probe or pat thereof being obtained from amplification of a nucleic acid sequence of a bacteria selected from the group consisting of *Bacteroides forsythus* strain ATCC 43037, *Porphyromonas gingivalis* strain ATCC 33277, *Prevotella intermedia* strain ATCC 25611 and *Prevotella nigrescens* strain NCTC 9336 with a primer selected from the group consisting of primers as set forth in SEQ ID NO:1, SEQ ID NO:2 and SEQ ID NO:3.

15. A diagnostic kit according to claim 14, wherein said primer pair is selected from the group consisting of primer pairs as set forth in SEQ ID NO:4 and SEQ ID NO:5; SEQ ID NO:6 and SEQ ID NO:7; SEQ ID NO:8 and SEQ ID NO:9; and SEQ ID NO:10 and SEQ ID NO:11.

16. The probe of claim 1 for the specific detection and identification of *Bacteroides forsythus*, wherein said probe has a nucleic acid sequence as set forth in SEQ ID NO:16.

17. The probe of claim 2 for the specific detection and identification of *Porphyromonas gingivalis*, wherein said probe has a nucleic acid sequence as set forth in SEQ ID NO:17.

18. The probe of claim 3 for the specific detection and identification of *Prevotella intermedia*, wherein said probe has a nucleic acid sequence as set forth in SEQ ID NO:18.

19. The probe of claim 4 for the specific detection and identification of *Prevotella nigrescens*, wherein said probe has a nucleic acid sequence as set forth in SEQ ID NO:19 or SEQ ID NO:20.

* * * * *

SEQUENCE LISTING ( 1 ) GENERAL INFORMATION:

( i i i ) NUMBER OF SEQUENCES: 20

( 2 ) INFORMATION FOR SEQ ID NO: 1:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "AP- PCR primer for B. forsythus"

( i i i ) HYPOTHETICAL: NO ( i v ) ANTI-SENSE: NO ( x i ) SEQUENCE DESCRIPTION: SEQ ID NO: 1:

C A G G C C C T T C         10

( 2 ) INFORMATION FOR SEQ ID NO: 2:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "AP- PCR primer for P.

gingivalis"

(iii) HYPOTHETICAL: YES (iv) ANTI-SENSE: YES (xi) SEQUENCE DESCRIPTION: SEQ ID NO: 2:

GTAAGGCCG                                                                                                                            9

(2) INFORMATION FOR SEQ ID NO: 3:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "AP- PCR primer for P. intermedia and P. nigrescens"

(iii) HYPOTHETICAL: NO (iv) ANTI-SENSE: NO (xi) SEQUENCE DESCRIPTION: SEQ ID NO: 3:

CAGCACCCAC                                                                                                                           10

(2) INFORMATION FOR SEQ ID NO: 4:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Specific PCR primer for B. forsythus"

(iii) HYPOTHETICAL: NO (iv) ANTI-SENSE: NO (xi) SEQUENCE DESCRIPTION: SEQ ID NO: 4:

ATGCTCCTGC TGGGTCTGTT                                                                                                                20

(2) INFORMATION FOR SEQ ID NO: 5:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "specific PCR primer for B. forsythus"

(iii) HYPOTHETICAL: NO (iv) ANTI-SENSE: YES (xi) SEQUENCE DESCRIPTION: SEQ ID NO: 5:

CGACACTTCG GATCGTTTAG                                                                                                                20

(2) INFORMATION FOR SEQ ID NO: 6:

(i) SEQUENCE CHARACTERISTICS:
      (A) LENGTH: 20 base pairs
      (B) TYPE: nucleic acid
      (C) STRANDEDNESS: single (D) TOPOLOGY: linear (ii) MOLECULE TYPE: other nucleic acid
(A) DESCRIPTION: /desc = "Specific PCR primer for P. gingivalis"

(iii) HYPOTHETICAL: NO (iv) ANTI-SENSE: NO (xi) SEQUENCE DESCRIPTION: SEQ ID NO: 6:

AATCGTAACG GGCGACACAC 20

(2) INFORMATION FOR SEQ ID NO: 7:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Specific PCR primer for P. gingivalis"

(iii) HYPOTHETICAL: NO (iv) ANTI-SENSE: YES (xi) SEQUENCE DESCRIPTION: SEQ ID NO: 7:

GGGTTGCTCC TTCATCACAC 20

(2) INFORMATION FOR SEQ ID NO: 8:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Specific PCR primer for P. intermedia"

(iii) HYPOTHETICAL: NO (iv) ANTI-SENSE: NO (xi) SEQUENCE DESCRIPTION: SEQ ID NO: 8:

CAGCACCCAC AACGATATGA 20

(2) INFORMATION FOR SEQ ID NO: 9:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Specific PCR primer for P. intermedia"

(iii) HYPOTHETICAL: NO (iv) ANTI-SENSE: YES (xi) SEQUENCE DESCRIPTION: SEQ ID NO: 9:

TTCCATCTTC TCTGCCTGTC 20

(2) INFORMATION FOR SEQ ID NO: 10:

-continued

```
       ( i ) SEQUENCE CHARACTERISTICS:
              ( A ) LENGTH: 24 base pairs
              ( B ) TYPE: nucleic acid
              ( C ) STRANDEDNESS: single
              ( D ) TOPOLOGY: linear ( i i ) MOLECULE TYPE: other nucleic acid
              ( A ) DESCRIPTION: /desc = "Specific PCR primer for P.
                    nigrescens"

( i i i ) HYPOTHETICAL: NO ( i v ) ANTI-SENSE: NO ( x i ) SEQUENCE DESCRIPTION: SEQ ID NO: 10:

TTATGTTACC CGTTATGATG GAAG                                                              24

( 2 ) INFORMATION FOR SEQ ID NO: 11:

( i ) SEQUENCE CHARACTERISTICS:
              ( A ) LENGTH: 24 base pairs
              ( B ) TYPE: nucleic acid
              ( C ) STRANDEDNESS: single
              ( D ) TOPOLOGY: linear ( i i ) MOLECULE TYPE: other nucleic acid
              ( A ) DESCRIPTION: /desc = "Specific PCR primer for P.
                    nigrescens"

( i i i ) HYPOTHETICAL: NO ( i v ) ANTI-SENSE: YES ( x i ) SEQUENCE DESCRIPTION: SEQ ID NO: 11:

ATGGCGAAAT AGGAATGAAA GTTA                                                              24

( 2 ) INFORMATION FOR SEQ ID NO: 12:

( i ) SEQUENCE CHARACTERISTICS:
              ( A ) LENGTH: 22 base pairs
              ( B ) TYPE: nucleic acid
              ( C ) STRANDEDNESS: single
              ( D ) TOPOLOGY: linear ( i i ) MOLECULE TYPE: other nucleic acid
              ( A ) DESCRIPTION: /desc = "Primer pair No. 1 for P.
                    intermedia"

( i i i ) HYPOTHETICAL: NO ( i v ) ANTI-SENSE: NO ( x i ) SEQUENCE DESCRIPTION: SEQ ID NO: 12:

AGTCCTTCGC TTTCTTGCTT AC                                                                22

( 2 ) INFORMATION FOR SEQ ID NO: 13:

( i ) SEQUENCE CHARACTERISTICS:
              ( A ) LENGTH: 22 base pairs
              ( B ) TYPE: nucleic acid
              ( C ) STRANDEDNESS: single
              ( D ) TOPOLOGY: linear ( i i ) MOLECULE TYPE: other nucleic acid
              ( A ) DESCRIPTION: /desc = "Primer pair No. 1 for P.
                    intermedia"

( i i i ) HYPOTHETICAL: NO ( i v ) ANTI-SENSE: YES ( x i ) SEQUENCE DESCRIPTION: SEQ ID NO: 13:

GAGTTCCTGC TTTTGTCTTT CA                                                                22
```

( 2 ) INFORMATION FOR SEQ ID NO: 14:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PCR primer pair No. 2 for
        P. intermedia"

( i i i ) HYPOTHETICAL: NO ( i v ) ANTI-SENSE: YES ( x i ) SEQUENCE DESCRIPTION: SEQ ID NO: 14:

ATTTCCATCT TCTCTGCCTG TC        22

( 2 ) INFORMATION FOR SEQ ID NO: 15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PCR primer pair No. 3 for
        P. intermedia"

( i i i ) HYPOTHETICAL: NO ( i v ) ANTI-SENSE: YES ( x i ) SEQUENCE DESCRIPTION: SEQ ID NO: 15:

AAGCAAGAAA GCGAAGGACT        20

( 2 ) INFORMATION FOR SEQ ID NO: 16:

( i ) SEQUENCE CHARACTERISTICS:
        ( A ) LENGTH: 392 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Target internal sequence
        of B. forsythus"

( i i i ) HYPOTHETICAL: NO ( i v ) ANTI-SENSE: NO ( x i ) SEQUENCE DESCRIPTION: SEQ ID NO: 16:

ATGCTCCTGC TGGGTCTGTT TGAGGTATTC GATACCGTAA TCGTGCTGCG CTTTAGTCCA    60

TGCAACGACT TCGGGATTTT CCTTATCTTC GAGCCAGCGG AACGGATCGG TGATCACCAC    120

GTTATGCAAC GTATCTTTTA CGGGTTTTTG AAGAGTCACC GGGGGGCGAA ACGCTACTTG    180

AGCGTAAGAG GTCACTGTCA TGGTCAAAGT AAGTGGAAAC ATGAAAAAAT TCTTCATCTN    240

CAATTGTATT TTTGAATAAG TTTGTTTTTG TGTNCAAACA TAGATAAAAA AGCTGAGATT    300

AAATATGGAA AAGAAGATAA ATCTCGGACG CGGTTTTCT TTTTCGGAGA AAATGATGTA    360

CCTTTGCATT TGCTAAACGA TCCGAAGTGT CG    392

( 2 ) INFORMATION FOR SEQ ID NO: 17:

( i ) SEQUENCE CHARACTERISTICS:

( A ) LENGTH: 593 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Target internal sequence for P. gingivalis"

( i i i ) HYPOTHETICAL: NO ( i v ) ANTI-SENSE: NO ( x i ) SEQUENCE DESCRIPTION: SEQ ID NO: 17:

| | | | | | | |
|---|---|---|---|---|---|---|
| AATCGTAACG | GGCGACACAC | CGGGTACCGC | CCGGAGATCG | GCCGCCAAAT | AGGACTGTGG | 60 |
| GACGAAAGCT | GTACGGAGCG | GAATATGATC | ACCGGTTCGG | ATTTCGCAGC | CCTCACCGAC | 120 |
| GAGGAACTGC | GCCCTCGGAT | AGGCGAACTG | CGTATCATGT | CCGCGCTCGT | CGATGGACAA | 180 |
| GGAAAGGCTT | GTACGCCTGC | TGCAGGAAGG | CTCGCGAAGG | TGGTGGCCGT | GACGGGCGAC | 240 |
| GGCACGAACG | ACGCTCCTGC | ACTCAACCGC | GCACAGGTGG | GCCTCTCGAT | GGGCGATGGC | 300 |
| ACTGCGTAGC | CAAAGAGGCG | AGCGACATCA | CCATTCTGGA | CAATTCTTTC | AGCAGCATTG | 360 |
| CCAAAGCCGT | TATGTGGGA | CGATCGCTTT | ATCGGAATAT | CCGCCGTTTT | ATCCTCTTTC | 420 |
| AGATGACCAT | CAACGTCGTG | GCCTGTATCA | TCGTTCTGAT | CGGCGCATTT | GTGGGTACGG | 480 |
| AGTCGCCCCT | TACCGTGACG | CAAATGCTGT | GGGTCAATCT | CATCATGGAC | ACTTTCGCCG | 540 |
| CCTTGTCCTT | GGCTTCGCTC | CCTCCCGACA | AGGGTGTGAT | GAAGGAGCAA | CCC | 593 |

( 2 ) INFORMATION FOR SEQ ID NO: 18:

( i ) SEQUENCE CHARACTERISTICS:
( A ) LENGTH: 754 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Target internal sequence of P. intermedia"

( i i i ) HYPOTHETICAL: NO ( i v ) ANTI-SENSE: NO ( x i ) SEQUENCE DESCRIPTION: SEQ ID NO: 18:

| | | | | | | |
|---|---|---|---|---|---|---|
| CAGCACCCAC | AACGATATGA | TCTGCCACAG | CTTTTGAACC | ATTATGTTCA | GCACTTACAC | 60 |
| TTGCCAACAA | CATTATATCG | TCCCATGGCA | AATAGCCAAC | TTTTGNCTCA | AGCCCGATAT | 120 |
| TGAACTTATC | GTGCCCGTTA | TAGTGCAAGT | CAAGACCTGT | CAAAGAAGCT | CCAAGGTAGC | 180 |
| CTTTACCCTC | TTGAAACTGT | GCATGAATAC | CTAATGATAA | TGTTAATCCT | AATAAAAGGA | 240 |
| GGGATAATTT | CTTCATCATA | ATAATACTGT | TATTGTAAAA | TCTATTTATT | GCTAAATTCC | 300 |
| ATTGACAAAG | GTAGTAGAAA | TATTTGAATT | ACAAAAATTA | TTGCCTATCT | TTGTGCCTGA | 360 |
| TTTGCAAATA | AGTCCTTCGC | TTTCTTGCTT | ACAAATATGC | TTTAAACGT | ATGAATAAAA | 420 |
| AATTAATTAC | ACTGATATTA | CTAAGCTGTC | TTCACGATAA | ATTGTTTTGC | ACAAACGGGC | 480 |
| GAAATATTTA | TAAATTGGGA | TACAAAACCT | TTCAAGAAAC | GTGAAACCCG | TGCTGTTTGG | 540 |
| CTAACTACTT | TGAACAATCT | TGACTGGCCA | AAGACATTTG | CAAACTCGGA | GNGAGGTATT | 600 |
| GAAAGACAAA | AGCAGGAACT | CATTGATATT | TTAGATAAAT | ATGTCGCTGC | AAACATTAAT | 660 |
| ACCGTTCTGT | TGCAAACGCG | TGTGCGTGCA | GCCACCATTT | ATCCGTCCAA | CATAGAACCT | 720 |
| TGGGACAAAT | GCTTGACAGG | CAGAGAAGAT | GGAA | | | 754 |

-continued ( 2 ) INFORMATION FOR SEQ ID NO: 19:

( i ) SEQUENCE CHARACTERISTICS:
        ( A ) LENGTH: 249 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "5'end of target internal sequence of P. negrescens"

( i i i ) HYPOTHETICAL: NO ( i v ) ANTI-SENSE: NO ( x i ) SEQUENCE DESCRIPTION: SEQ ID NO: 19:

```
TTATGTTACC  CGTTATGATG  GAAGTAGTTG  GGCGTTGTGT  TGCTATAATC  ATGTGAATGC      60
CTACCGCACG  CGCCAGCTGG  GCGATACGGG  TGATAGGCAT  TTCAATTTCT  TTTCCAGCGG     120
TAAGGATAAG  GTCTCCGAAC  TCATCAATGA  TGACAACGAT  GTACGGTATG  AACTCGTGTC     180
CTCCCGCAGG  ACTAAGCTGA  TGGCTAAGGA  ACTTCTTGTT  ATACTCTTTT  ATATTGCGCG     240
CTCCTGTAG                                                                 249
```

( 2 ) INFORMATION FOR SEQ ID NO: 20:

( i ) SEQUENCE CHARACTERISTICS:
        ( A ) LENGTH: 142 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "3'end of target internal sequence of P. negrescens"

( i i i ) HYPOTHETICAL: NO ( i v ) ANTI-SENSE: NO ( x i ) SEQUENCE DESCRIPTION: SEQ ID NO: 20:

```
AAATTAAGGG  TTGGATACTN  CCAATTGGGG  AAAGGTTCGT  GTGGATTAAT  AGGTGTTNCA      60
AGGTCTGTCG  TGCCTGCCAC  CCCCTTACCT  TGTGCCTTTT  CCAACCCGAC  AGGGACATTA     120
ACTTTCATTC  CTATTTCGCC  AT                                                142
```